United States Patent
Urueta et al.

(12) 
(10) Patent No.: US 6,367,110 B1
(45) Date of Patent: Apr. 9, 2002

(54) SELF-CLEANING HOLSTER FOR ELECTROCAUTERY TIP

(76) Inventors: Joshua M. Urueta, 7010 S. Santa Clara Ave., Tucson, AZ (US) 85706; R. Wilfrido Urueta, 3781 W. Meadow Briar Dr., Tucson, AZ (US) 85741

( * ) Notice: Subject to any disclaimer, the term of this patent is extended or adjusted under 35 U.S.C. 154(b) by 0 days.

(21) Appl. No.: 09/389,833

(22) Filed: Sep. 3, 1999

(51) Int. Cl.[7] .......................... A46B 11/00; A46B 15/00; A47L 25/00
(52) U.S. Cl. .......................... 15/160; 15/218; 15/218.1; 15/210.1; 206/349; 206/438
(58) Field of Search .................... 15/160, 218, 218.1, 15/220.4, 221, 210.1, 104.92, 114, 21.2; 206/365, 349, 438; 24/3.9

(56) References Cited

U.S. PATENT DOCUMENTS

| | | | |
|---|---|---|---|
| D231,031 S | * | 3/1974 | Hinnenkamp |
| 3,986,648 A | | 10/1976 | Antonini et al. ............. 224/5 H |
| 4,087,878 A | * | 5/1978 | Grieshaber et al. ............ 15/160 |
| 4,170,234 A | | 10/1979 | Graham .................. 128/303.14 |
| 4,196,734 A | | 4/1980 | Harris ...................... 128/303.1 |
| 4,245,367 A | * | 1/1981 | Stoute ........................ 15/210.1 |
| 4,547,923 A | | 10/1985 | DeVries et al. ............ 15/104 R |
| D282,684 S | * | 2/1986 | Cline ........................... D24/29 |
| 5,222,271 A | * | 6/1993 | Eganhouse .................... 15/160 |
| 5,234,428 A | | 8/1993 | Kaufman ..................... 606/45 |
| 5,471,706 A | * | 12/1995 | Wallock et al. .......... 15/104.92 |
| 5,533,618 A | | 7/1996 | Pickels, Jr. .................. 206/363 |
| 5,666,684 A | * | 9/1997 | Cussen ........................ 15/160 |
| 5,666,686 A | * | 9/1997 | Dao ............................ 15/218 |

* cited by examiner

Primary Examiner—Gary K. Graham
(74) Attorney, Agent, or Firm—David W. Collins

(57) ABSTRACT

A self-cleaning holster for holding an electrosurgical instrument and for cleaning a blade secured to the electrosurgical instrument is provided. The holster has a portion for securely supporting the holder portion of the instrument, as well as a portion for securely supporting and cleaning the blade. A separate blade-cleaning portion is provided for cleaning the blade during surgery.

38 Claims, 1 Drawing Sheet

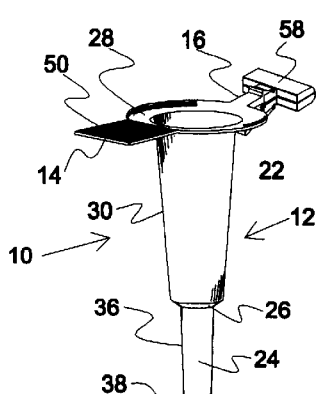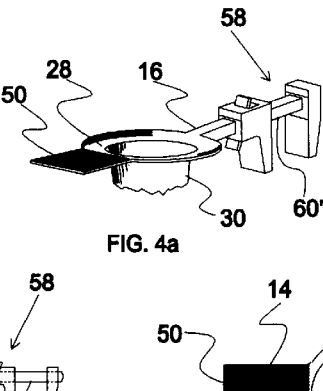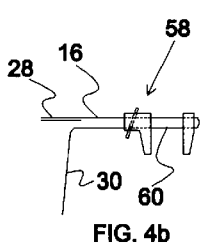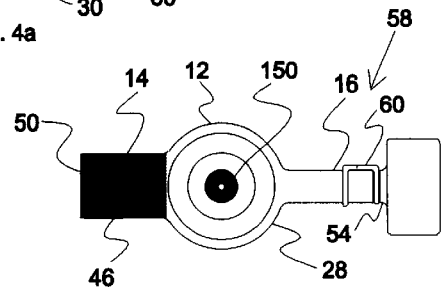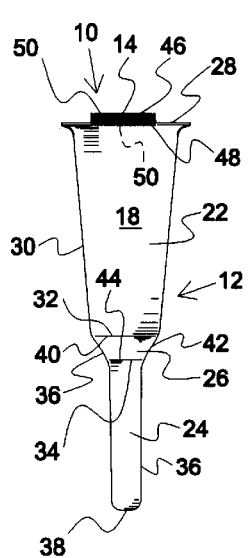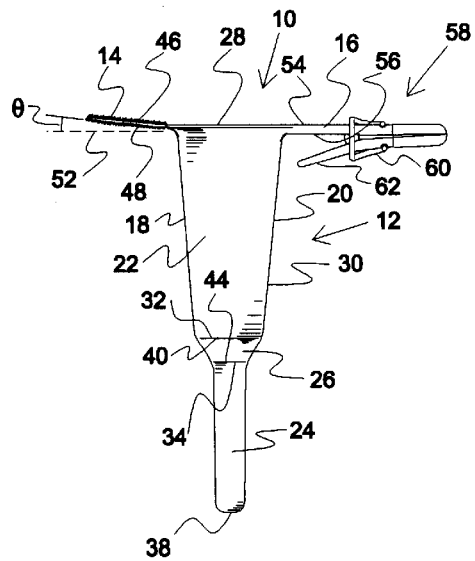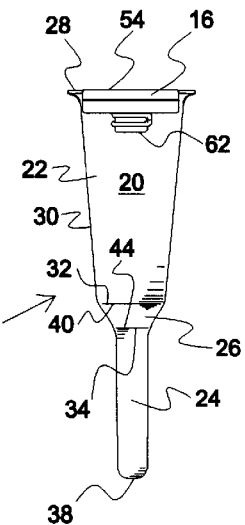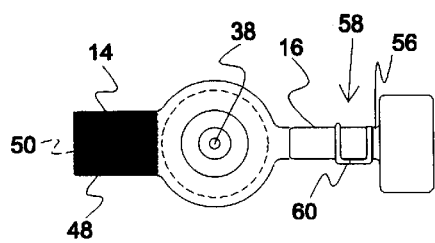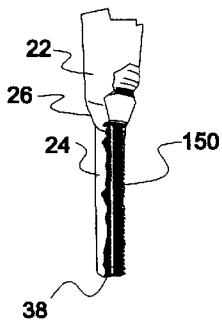

SELF-CLEANING HOLSTER FOR ELECTROCAUTERY TIP

TECHNICAL FIELD

The present invention is directed to electrosurgery/cautery apparatus, and, more particularly, to a holster for holding and cleaning electrocautery tips used in electrosurgery.

BACKGROUND ART

During electrosurgery, electrocautery knives are used for cauterization as well as cutting, for example, to destroy dead tissue, to stop bleeding, and to prevent the spread of infection. In this process, the blade, or tip, of the electrocautery knife accumulates debris and should be frequently cleaned to remove unwanted tissue and maintain a clean incision.

In the past, sandpaper pads or a single slot molded into the edge of a holster in which the knife is kept have been used to clean electrocautery blades.

An electrosurgery/cautery system and method are disclosed in U.S. Pat. No. 4,196,734, issued on Apr. 8, 1980, to F. W. Harris. This patent is an example of electro-surgery apparatus. However, no holster or cleaning mechanism for the electrocautery tips is disclosed.

A surgical knife cleaner is disclosed in U.S. Pat. No. 4,547,923, issued on Oct. 22, 1985, to J. H. DeVries et al. In this patent, a readily attachable base has a cradle to retain a closely coiled strand on an axis parallel to the base. The cradle has edges to limit the introduction of the knife blade in the direction transverse to the axis of the coil and to clean the edge of the knife blade. However, the coiled strand is metal, and repeated insertion of a coated electrocautery tip thereinto will cause degradation of the coating and thus reduced effectiveness of the blade.

A disposable electrocautery/cutting instrument with integral smoke evacuation is disclosed in U.S. Pat. No. 5,234,428, issued on Aug. 10, 1993 to D. L. Kaufrnan. This patent is an example of electrosurgery apparatus, specifically, the pencil portion which secures and holds the electrocautery tip, or blade. However, no holster or cleaning mechanism for the electrocautery tips is disclosed.

A surgical holster is disclosed in U.S. Pat. No. 5,533,618, issued on Jul. 9, 1996, to R. F. Pickels, Jr. The surgical holster is suitable for carrying elongated surgical instruments, such as for use with a laparascope when carrying out Minimal Invasive Surgery. The surgical holster has a backing plate which supports a plurality of detachable receptacle members contained on the backing plate in fixed engagement. The device is made of a transparent thermoplastic which is electrically insulating, nonflammable, and which can be sterilized at temperatures above 300° F. However, the holster has no provision for cleaning electrocautery tips.

Gold-plated electrosurgical tips are disclosed in U.S. Pat. No. 5,643,256, issued on Jul. 1, 1997, and U.S. Pat. No. 5,885,218, issued on Mar. 23, 1999, both to R. Wilfrido Urueta. Both patents are specifically directed to improved electrosurgical tips, which reduce adhesion of tissue debris to the tips and provide more efficient cutting and cauterization of tissue with less power consumption.

A need remains for a holster for holding electrosurgical knives as well as providing a mechanism for cleaning the tips during surgery.

DISCLOSURE OF INVENTION

In accordance with the present invention, a self-cleaning holster for holding an electrosurgical instrument and for cleaning a blade secured to the electrosurgical instrument is provided. The holster comprises:

(a) a unitary receptacle comprising a first portion, a transition portion, and a second portion, the unitary receptacle having a front and a back, the unitary receptacle comprising
  (i) the first portion having an open top, a downwardly-depending, larger, tapered cylindrical side, and an open bottom,
  (ii) the second portion having an open top, a downwardly-depending, cylindrical side, and a closed bottom, and
  (iii) the transition portion comprising an open top, a downwardly-depending, smaller, tapered cylindrical side, and an open bottom, the open bottom of the first portion terminating at the open top of the transition portion and the open top of the second portion terminating at the open bottom of the transition portion, the transition portion thereby providing a transition from the first portion to the second portion;
(b) a first outwardly-extending member integral with the unitary receptacle and extending out from the front of the cylindrical side of the first portion at its top, the first outwardly-extending member having a top surface and a bottom surface, at least the top surface provided with a blade-cleaning material;
(c) a second outwardly-extending member integral with the unitary receptacle and extending out from the back of the cylindrical side of the first portion at its top, the second outwardly-extending member having a top surface and a bottom surface and an attachment means secured to the top surface and the bottom surface; and
(d) a cylinder of a blade-cleaning material contained in the second portion of the receptacle.

The holster of the present invention is directed, among other things, to holding electrosurgical knives and cleaning the electrosurgical tips associated therewith, such as the tips disclosed in the two patents to Urueta referenced above (U.S. Pat. No. 5,643,256 and U.S. Pat. No. 5,885,218), although the holster is not limited to these electrosurgical tips, but may be employed with other electrosurgical tips.

Other objects, features, and advantages of the present invention will become apparent upon consideration of the following detailed description and accompanying drawings, in which like reference designations represent like features throughout the FIGURES.

BRIEF DESCRIPTION OF THE DRAWINGS

The drawings referred to in this description should be understood as not being drawn to scale except if specifically noted.

FIG. 1 is a perspective view of the self-cleaning holster of the present invention;

FIG. 2 is a top plan view of the self-cleaning holster for electrocautery tip of the present invention;

FIG. 3 is a front elevational view thereof;

FIG. 4 is a left side elevational view thereof;

FIG. 4a is a perspective view of a portion of the self-cleaning holster, depicting an alternate clamping embodiment;

FIG. 4b is a side elevational view of the alternate clamping embodiment shown in FIG. 4a;

FIG. 5 is a rear elevational view thereof;

FIG. 6 is a bottom plan view thereof; and

FIG. 7 is a cut-away view of the lower portion of the holster.

BEST MODES FOR CARRYING OUT THE INVENTION

Reference is now made in detail to a specific embodiment of the present invention, which illustrates the best mode presently contemplated by the inventors for practicing the invention. Alternative embodiments are also briefly described as applicable.

Electrocautery instruments are often employed in surgery to perform incisions in the flesh of a patient. The electrocautery instrument both cuts flesh and simultaneously cauterizes it, providing a relatively clean cut with minimal bleeding. Examples of electrocautery surgery include cardiovascular, ophthalmology, neurosurgery, dermatology, and plastic surgery, although the self-cleaning holster of the present invention is not limited to these specific procedures.

Electrocautery instruments, also known as electrosurgical instruments, typically comprise an insulating handle that fits in the hands of the operating surgeon and an electrically-conducting electrocautery blade or tip secured to one end of the handle. The electrocautery blade or tip is electrically energized to an electrical potential for cutting and cauterizing flesh. The blade may be uni-polar or bi-polar. Such electrocautery instruments are well-known and do not form a part of this invention, except to the extent that they are supported and cleaned by the self-cleaning holster described and claimed herein.

During electrocautery surgery, the operating surgeon often needs to clean the blade of particles of flesh that adhere to the blade. Further, the operating surgeon needs to put the instrument down temporarily to perform other tasks. In both instances, the blade is electrically "hot"; that is, an electrical potential exists on the electrically-conducting blade. Laying the electrocautery instrument down on a surface could present hazards to operating room personnel if the surface is also electrically-conducting. Further, such a placement could expose operating personnel to potential hazards by someone inadvertently picking up the instrument by the blade instead of the handle. The present invention solves these problems.

Turning now to the Figures, the self-cleaning holster 10 of the present invention is shown. The holster 10 comprises three main portions: a unitary receptacle 12, a first outwardly-extending member 14 integral with the unitary receptacle, and a second outwardly-extending member 16, also integral with the unitary receptacle.

The unitary receptacle 12 has a front 18 and a back 20. The unitary receptacle further comprises a first portion 22, a second portion 24, and a transition portion 26.

The first portion 22 has an open top 28, a downwardly-depending, larger, tapered cylindrical side 30, and an open bottom 32. The second portion 24 has an open top 34, a downwardly-depending, cylindrical side 36, and a closed bottom 38. The transition portion 26 comprises an open top 40, a downwardly-depending, smaller, tapered cylindrical side 42, and an open bottom 44. The open bottom 32 of the first portion 22 terminates at the open top 40 of the transition portion 26. The open top 34 of the second portion 24 terminates at the open bottom 44 of the transition portion 26. The transition portion 26 thereby provides a transition from the first portion 22 to the second portion 24.

The first outwardly-extending member 14 extends out from the front 18 of the cylindrical side 30 of the first portion 22 at its top 28. The first outwardly-extending member 14 has a top surface 46 and a bottom surface 48. At least the top surface 46 is provided with a blade-cleaning material 50. However, the bottom surface 48 may also be provided with the blade-cleaning material 50. Although the first outwardly-extending member 14 may extend horizontally from the top 28, advantageously, it is angled upward at an angle θ of about 3° to 10° from a horizontal plane 52 extending across the top. The slight angle facilitates movement of debris scraped from the blade into the interior of the holster 10. The blade-cleaning material 50 comprises a rough surface formed on the top surface 46 (and bottom surface 48, if desired), as described more fully below.

The presence of blade-cleaning material on the top surface 46 (and, optionally, the bottom surface 48), permits the surgeon to clean the blade, or tip, during surgery as it becomes covered with flesh and other debris, using a simple wiping motion of the blade over the blade-cleaning material.

The second outwardly-extending member 16 extends out from the back 20 of the cylindrical side 30 of the first portion 22 at its top 28. The second outwardly-extending member 16 has a top surface 54, a bottom surface 56 and an attachment means 58 secured to the top surface and the bottom surface. The attachment means 58 may comprise a spring-loaded clamp or coil clamp 60, sized to clamp around the edge of a Mayo instrument table. The attachment means 58 comprises the same material as the holster 10, but may be of a denser variety for increased strength. The attachment means 58 includes a releasable clip portion 62, which advantageously is mounted underneath the second outwardly extending member 16 on bottom surface 56. The releasable clip portion 62 is mounted so that the handle thereof is interior to the attachment means relative to the spring loaded clamp or coil clamp 60. The underneath, inward mounting places the clip portion 62 out of the way so that accidental release of the holster 10 from its attachment is minimized.

The attachment means may comprise a flat paddle clip 60, as shown in FIG. 4, or a spring-loaded, wide-base C-clamp 60', as shown in FIGS. 4a–4b. The attachment means 58 provides a pressure of about 10 oz/in$^2$ on each clamping face, as an example.

The attachment means 58 permits the holster 10 to be securely attached to a surface chosen by the operating surgeon, such as an instrument table, the operating table, a near-by support, or suitable attachment location (not shown).

Bristles of a blade-cleaning material 150 are contained in the second portion 24 of the receptacle 12. The blade-cleaning material 150 may be the same as the blade-cleaning material 50 secured to the first outwardly-extending member 14 or different. Preferably, for ease of production, the blade-cleaning material 150 is the same as the blade-cleaning material 50. The blade-cleaning material 150 is oriented so that the blade-cleaning operation takes place by insertion of an electrocautery tip (not shown) into the interior of the cylinder 24.

The unitary receptacle 12, the first outwardly-extending member 14, and the second outwardly-extending member 16 are all one piece, or integral, and are formed in one forming operation, using an inert material, preferably a polymeric material, such as, but not limited to, nylon, polyethylene, polypropylene (e.g., high density polypropylene), polytetrafluoroethylene, and other such plastics commonly used in operating rooms. A typical wall thickness for all parts of the unitary receptacle 12 is about 0.025 to 0.05 inch for providing sufficient sturdiness for the receptacle to be durable and not yield or bend under reasonable externally-applied pressure.

The inner diameter of the first portion 22 of the unitary receptacle 12 is sized to approximate the diameter of the handle of the electrocautery knife (not shown), and the taper of the side 30 serves to support the handle so that the electrocautery tip (not shown) penetrates into the second portion 24, but is not simply allowed to drop into the second portion, thereby possibly causing damage to the tip.

The inner diameter of the second portion 24 is sized, together with blade-cleaning material 150, to actively clean the tip during insertion and removal of the electrocautery knife, without causing undue restriction on insertion and removal. Thus, the simple act of placing the knife in the holster serves to both securely hold and support the knife while simultaneously cleaning the tip.

The blade-cleaning material 50, 150 preferably comprises the same material as the unitary receptacle 12, and is formed in the same operation as the unitary receptacle. In this way, processing costs are minimized, since no separate operations, such as adhering the blade-cleaning material 50, 150 to the first outwardly-extending member 14 and the interior of the second portion 24 of the receptacle 12, respectively, are required.

The blade-cleaning material 50, as mentioned above, comprises a rough surface of a plastic material, preferably the same plastic material as the holster 10 and is formed during the holster forming operation. A suitable pattern is a cross-hatch, comprising peaks and valleys, in which the peaks of plastic scrape off debris from the blade and the valleys collect it. Bristles of the plastic material may alternately be used; exemplary dimensions are bristles about 0.03 inch long and about 0.015 inch thick.

The blade-cleaning material 150, as mentioned above, comprises bristles of a plastic material. The length of the bristles 150 is typically about ⅖ the inside diameter of the second portion 24. The bristles have a packing density of about 400 bristles per square inch, although the invention is not so limited.

Following use in an electrocautery operating procedure, the holster is discarded, so that for each patient operated on, a new holster is used.

INDUSTRIAL APPLICABILITY

The self-cleaning holster disclosed herein is expected to find use in electrosurgery for the storing of electrocautery instruments and the cleaning of electrocautery tips attached thereto.

Thus, there has been disclosed a self-cleaning holster for holding an electrocautery knife and for cleaning an electrocautery tip attached thereto. It will be readily apparent to those skilled in this art that various changes and modifications of an obvious nature may be made, and all such changes and modifications are considered to fall within the scope of the present invention, as defined by the appended claims.

What is claimed is:

1. A self-cleaning holster for holding and cleaning an electrosurgical instrument comprising a handle and a blade, said holster comprising:
   (a) a unitary receptacle comprising (i) an upper portion, said upper portion having a top and configured to hold and support said handle, said upper portion further having a first outwardly-extending member and a second outwardly-extending member, both extending outwardly from said top, and (ii) a lower portion, attached to said upper portion and including a first blade-cleaning material therein, for cleaning said blade;
   (b) a second blade-cleaning material secured to said first outwardly-extending member; and
   (c) a clamping attachment means secured to said second outwardly-extending member for attaching said self-cleaning holster to a clamping surface.

2. The self-cleaning holster of claim 1 wherein said unitary receptacle and said first and second outwardly-extending members comprise a plastic selected from the group consisting of nylon, polyethylene, polypropylene, and polytetrafluoroethylene.

3. The self-cleaning holster of claim 2 wherein said plastic consists essentially of high density polypropylene.

4. The self-cleaning holster of claim 2 wherein said first blade-cleaning material and said second blade-cleaning material both comprise the same material as said unitary receptacle.

5. The self-cleaning holster of claim 4 wherein said first and second blade-cleaning materials consist essentially of bristles of said plastic.

6. The self-cleaning holster of claim 5 wherein said bristles of said second blade-cleaning material have a length that is about ⅖ of a diameter of said lower portion.

7. The self-cleaning holster of claim 6 wherein said bristles have a packing density in a range of about 400 per square inch.

8. The self-cleaning holster of claim 5 wherein said bristles of said first blade-cleaning material have a length of about 0.030 inch and a thickness of about 0.015 inch.

9. The self-cleaning holster of claim 4 wherein said first blade-cleaning material comprises a rough surface, comprising a plurality of peaks and valleys.

10. The self-cleaning holster of claim 1 wherein said attachment means secured to said second outwardly-extending member comprises a clamp having two opposed faces for attaching said holster to a surface.

11. The self-cleaning holster of claim 10 wherein said clamp is a flat paddle clip.

12. The self-cleaning holster of claim 10 wherein said clamp is a spring-loaded C-clamp.

13. The self-cleaning holster of claim 10 wherein said clamp includes a spring to urge said two opposed faces in clamping arrangement to said surface.

14. A self-cleaning holster for holding an electrosurgical instrument and for cleaning a blade secured to said electrosurgical instrument, said holster comprising:
   (a) a unitary receptacle comprising a first portion, a transition portion, and a second portion, said unitary receptacle having a front and a back, said unitary receptacle comprising
      (i) said first portion having an open top, a downwardly-depending, larger, tapered cylindrical side, and an open bottom,
      (ii) said second portion having an open top, a downwardly-depending, cylindrical side, and a closed bottom, and
      (ii) said transition portion comprising an open top, a downwardly-depending, smaller, tapered cylindrical side, and an open bottom, said open bottom of said first portion terminating at said open top of said transition portion and said open top of said second portion terminating at said open bottom of said transition portion, said transition portion thereby providing a transition from said first portion to said second portion;
   (b) a first outwardly-extending member integral with said unitary receptacle and extending out from said front of said cylindrical side of said first portion at its top, said first outwardly-extending member having a top surface and a bottom surface, at least said top surface provided with a blade-cleaning material;

(c) a second outwardly-extending member integral with said unitary receptacle and extending out from said back of said cylindrical side of said first portion at its top, said second outwardly-extending member having a top surface and a bottom surface and an attachment means secured to said top surface and said bottom surface; and (d) a cylinder of said blade-cleaning material contained in said second portion of said receptacle.

15. The self-cleaning holster of claim 14 wherein said first outwardly-extending member extends from said front of said cylindrical side of said first portion at its top at an angle of 3° to 10°, relative to a horizontal plane extending across said top of said first portion.

16. The self-cleaning holster of claim 14 wherein said unitary receptacle and said first and second outwardly-extending members comprise a plastic selected from the group consisting of nylon, polyethylene, polypropylene, and polytetrafluoroethylene.

17. The self-cleaning holster of claim 16 wherein said plastic consists essentially of high density polypropylene.

18. The self-cleaning holster of claim 14 wherein said blade-cleaning material formed on said first outwardly-extending member and said blade-cleaning material contained in said second portion of said receptacle both comprise the same material as said unitary receptacle and said first and second outwardly-extending members.

19. The self-cleaning holster of claim 18 wherein said first and second blade-cleaning materials consist essentially of bristles of said plastic.

20. The self-cleaning holster of claim 19 wherein said bristles of said second blade-cleaning material have a length that is about ⅖ of a diameter of said lower portion.

21. The self-cleaning holster of claim 20 wherein said bristles have a packing density in a range of about 400 per square inch.

22. The self-cleaning holster of claim 19 wherein said bristles of said first blade-cleaning material have a length of about 0.030 inch and a thickness of about 0.015 inch.

23. The self-cleaning holster of claim 18 wherein said first blade-cleaning material comprises a rough surface, comprising a plurality of peaks and valleys.

24. The self-cleaning holster of claim 14 wherein said attachment means secured to said second outwardly-extending member comprises a clamp having two opposed faces for attaching said holster to a surface.

25. The self-cleaning holster of claim 24 wherein said clamp is a flat paddle clip.

26. The self-cleaning holster of claim 24 wherein said clamp is a spring-loaded C-clamp.

27. The self-cleaning holster of claim 24 wherein said clamp includes a spring to urge said two opposed faces in clamping arrangement to said surface.

28. A self-cleaning holster for holding and cleaning an electrosurgical instrument comprising a handle and a blade, said holster comprising:

(a) a unity receptacle comprising (i) an upper portion, said upper portion having a top and configured to hold and support said handle, and (ii) a lower portion, attached to said upper portion and including a first blade-cleaning material therein, for cleaning said blade;

(b) a second blade-cleaning material secured to said upper portion near its top; and (c) a clamping attachment means also secured to said upper portion near its top for attaching said self-cleaning holster to a clamping surface, wherein said attachment means comprises a clamp having two opposed faces for attaching said holster to a surface and wherein said clamp includes a spring to urge said two opposed faces in clamping arrangement to said surface.

29. The self-cleaning holster of claim 28 wherein said unitary receptacle comprises a plastic selected from the group consisting of nylon, polyethylene, polypropylene, and polytetrafluoroethylene.

30. The self-cleaning holster of claim 29 wherein said plastic consists essentially of high density polypropylene.

31. The self-cleaning holster of claim 29 wherein said first blade-cleaning material and said second blade-cleaning material both comprise the same material as said unitary receptacle.

32. The self-cleaning holster of claim 31 wherein said first and second blade-cleaning materials consist essentially of bristles of said plastic.

33. The self-cleaning holster of claim 32 wherein said bristles of said second blade-cleaning material have a length that is about ⅖ of a diameter of said lower portion.

34. The self-cleaning holster of claim 33 wherein said bristles have a packing density in a range of about 400 per square inch.

35. The self-cleaning holster of claim 32 wherein said bristles of said first blade-cleaning material have a length of about 0.030 inch and a thickness of about 0.015 inch.

36. The self-cleaning holster of claim 31 wherein said first blade-cleaning material comprises a rough surface, comprising a plurality of peaks and valleys.

37. The self-cleaning holster of claim 28 wherein said clamp is a flat paddle clip.

38. The self-cleaning holster of claim 28 wherein said clamp is a spring-loaded C-clamp.

* * * * *